United States Patent [19]
Khuri-Yakub et al.

[11] Patent Number: 4,995,259
[45] Date of Patent: Feb. 26, 1991

[54] ACOUSTIC MICROSCOPE SURFACE INSPECTION SYSTEM AND METHOD

[75] Inventors: Butrus T. Khuri-Yakub, Palo Alto, Calif.; Philippe Parent, Chilly-Mazarin, France; Paul A. Reinholdtsen, Seattle, Wash.

[73] Assignee: The Board of Trustees of the Leland Stanford Junior University, Stanford, Calif.

[21] Appl. No.: 320,950

[22] Filed: Mar. 9, 1989

[51] Int. Cl.⁵ .............................................. G01N 29/06
[52] U.S. Cl. ........................................ 73/593; 73/606
[58] Field of Search .................. 73/640, 606, 593, 620

[56] References Cited

U.S. PATENT DOCUMENTS

| | | | |
|---|---|---|---|
| 4,179,936 | 12/1979 | Bennett et al. | 73/606 |
| 4,503,708 | 3/1985 | Kino et al. | 73/606 |
| 4,541,281 | 9/1985 | Chubachi et al. | 73/602 |
| 4,694,699 | 9/1987 | Cheeke | 73/606 |
| 4,801,020 | 1/1989 | Rogne et al. | 73/105 |

FOREIGN PATENT DOCUMENTS 0019555  2/1983  Japan ...................................... 73/606

Primary Examiner—Hezron E. Williams
Assistant Examiner—Rose Finley
Attorney, Agent, or Firm—Flehr, Hohbach, Test, Albritton & Herbert

[57] ABSTRACT

An acoustic microscope surface inspection system and method in which pulses of high frequency electrical energy are applied to a transducer which forms and focuses acoustic energy onto a selected location on the surface of an object and receives energy from the location and generates electrical pulses. The phase of the high frequency electrical signal pulses are stepped with respected to the phase of a reference signal at said location. An output signal is generated which is indicative of the surface of said selected location. The object is scanned to provide output signals representative of the surface at a plurality of surface locations.

11 Claims, 5 Drawing Sheets

ACOUSTIC MICROSCOPE SURFACE INSPECTION SYSTEM AND METHOD

This work was supported by the Department of Energy under Contract No. DE-FG03-84ER45157

BRIEF DESCRIPTION OF THE INVENTION

This invention relates generally to an acoustic microscope surface inspection system and method for detecting small surface defects and more particularly to an acoustic microscope surface inspection system and method capable of detecting surface defects a few micrometers in depth. The system described is particularly adapted to inspection of balls for ball bearings.

BACKGROUND OF THE INVENTION

As new material such as ceramics are gaining acceptance in industry, it becomes critical to develop inspection methods for evaluation of their surface characteristics. One of the potential applications of ceramic materials is for balls for ball bearings. Balls in such bearings are subject to high dynamic stress and due to the brittleness of the ceramics it is important to inspect each ball and be able to detect surface and subsurface cracks ten micrometers in size, or smaller. It is essential to be able to detect such cracks using a fast system that allows full coverage of the bearing.

There are basically three types of surface defects. The first type are the fissures that exist near the surface and perpendicular to it. These cracks can easily be detected using surface acoustic waves which are very sensitive to this kind of perturbation.

The second type of defects are surface gouges which are shallow but relatively large, typically 10 micrometers or more in size. These are once again very easily detected by measuring the phase of the acoustic signal reflected from the bearing at the location of the defect. For an operating frequency of 120 MHz, where the wavelength in water is about 12 micrometers, one is able to image these defects even if their depths do not exceed 0.5 micrometers which corresponds to a phase variation of 30°, and without particular precautions concerning scanner vibrations.

The last kind of defect includes shallow cracks of small width with smooth corners. They are the most difficult to detect because they are insensitive to surface wave and are small compared to the spot size of the focused acoustic beam. Their size can be in the order of one micrometer while the beam size in the 100 MHz range is at least an order of magnitude larger.

SUMMARY AND OBJECTS OF THE INVENTION

It is a general object of the present invention to provide an acoustic microscope system and method which is capable of detecting surface defects in the order of a few micrometers deep.

It is another object of the present invention to provide an acoustic microscope which uses a tone burst of high frequency energy to excite an acoustic transducer and makes phase measurements of reflected waves with high accuracy.

It is another object of the present invention to provide an apparatus and method in which the object is excited with bursts of acoustic energy and the phase and amplitude of reflected and surface waves are converted to an electrical signal which is compared to a reference to provide indication of the state of the surface.

It is another object of the present invention to provide an acoustic microscope system for inspecting the surface of a sphere such as a ball bearing ball.

The foregoing and other objects of the invention are achieved by an inspection system which includes means for generation of a high frequency signal, a transducer for receiving bursts of said high frequency signal and generate and focus an acoustic wave at selected locations onto the surface of an object being inspected and which receives acoustical waves emanating from said location and generates an output signal. Means are included for generating a reference signal which is compared to the output signal to provide an output signal indicative of the relative phase and amplitude of the reflected signal and the referenced signal. The inspection system also includes means for mounting and rotating a bearing ball in cooperation with the transducer to present the complete ball surface to the transducer.

The invention will be more clearly understood from the following description read in conjunction with the accompanying drawings.

DESCRIPTION OF PREFERRED EMBODIMENT

Generally in accordance with the present invention an acoustic transducer generates acoustic waves responsive to high frequency input signals which impinge upon the object at a predetermined location and receives acoustic waves emanating from the location and generates electrical signals. The transducer alternately serves to receive electrical energy and transmit acoustical pulses and to receive echo acoustic pulses and generate electrical pulses.

Figure 1:
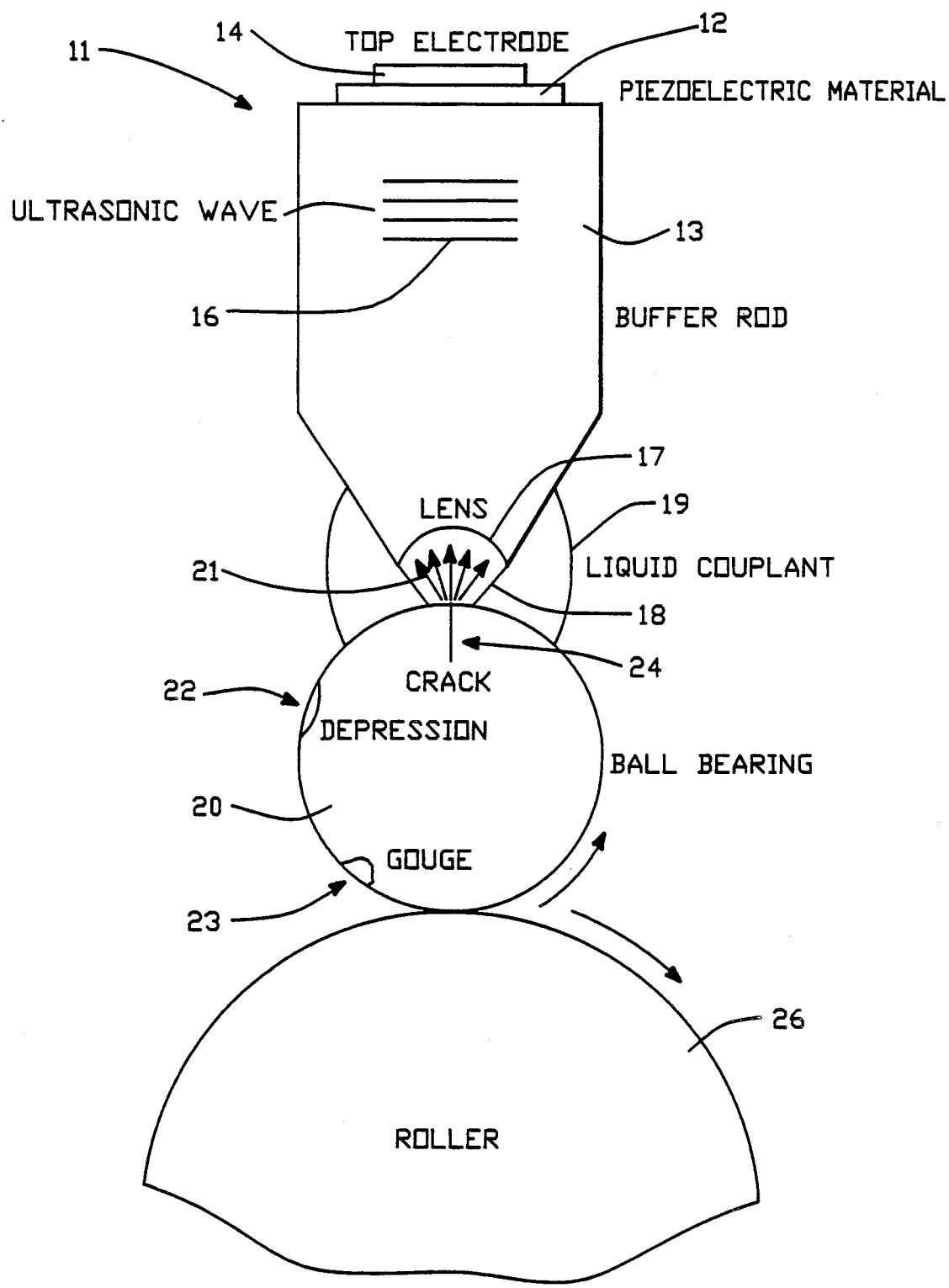
FIG. 1 shows the acoustic transducer cooperating with an associated ceramic bearing ball.

FIG. 1 shows a transducer assembly 11 including a piezoelectric transducer 12 in intimate contact with a buffer rod 13 and an electrode 14 contacting the other surface. The transducer generates ultrasonic waves 16 which travel towards the lens 17 in response to an electrical signal input. The ultrasonic waves are focused to form an acoustic beam 18. Acoustical waves are reflected and emitted by the object and received by the lens. An output electrical signal is generated in response to the acoustic waves received by the lens and transmitted to the piezoelectric member. The lens 17, which may be a spherical lens, focuses the acoustic waves at a particular location.

In FIG. 1 the waves travel through a liquid couplant 19 and are focused on the surface of the bearing ball 20. The arrows 21 show the echo acoustic energy which is reflected from the surface or which emanates as surface waves. The bearing ball shows the three types of defects previously described, namely, a depression 22, a gouge 23 and a deep crack 24. The bearing ball is rotated by a roller 26 to present various points along an equator. The roller is then translated to rotate the ball and present a different equator. A suitable ball bearing drive system will be described with reference to FIG. 4. By controlling rotation and translation of the roller and the pulse frequency the total surface of the bearing is presented to the transducer for inspection over a predetermined time.

Figure 2:
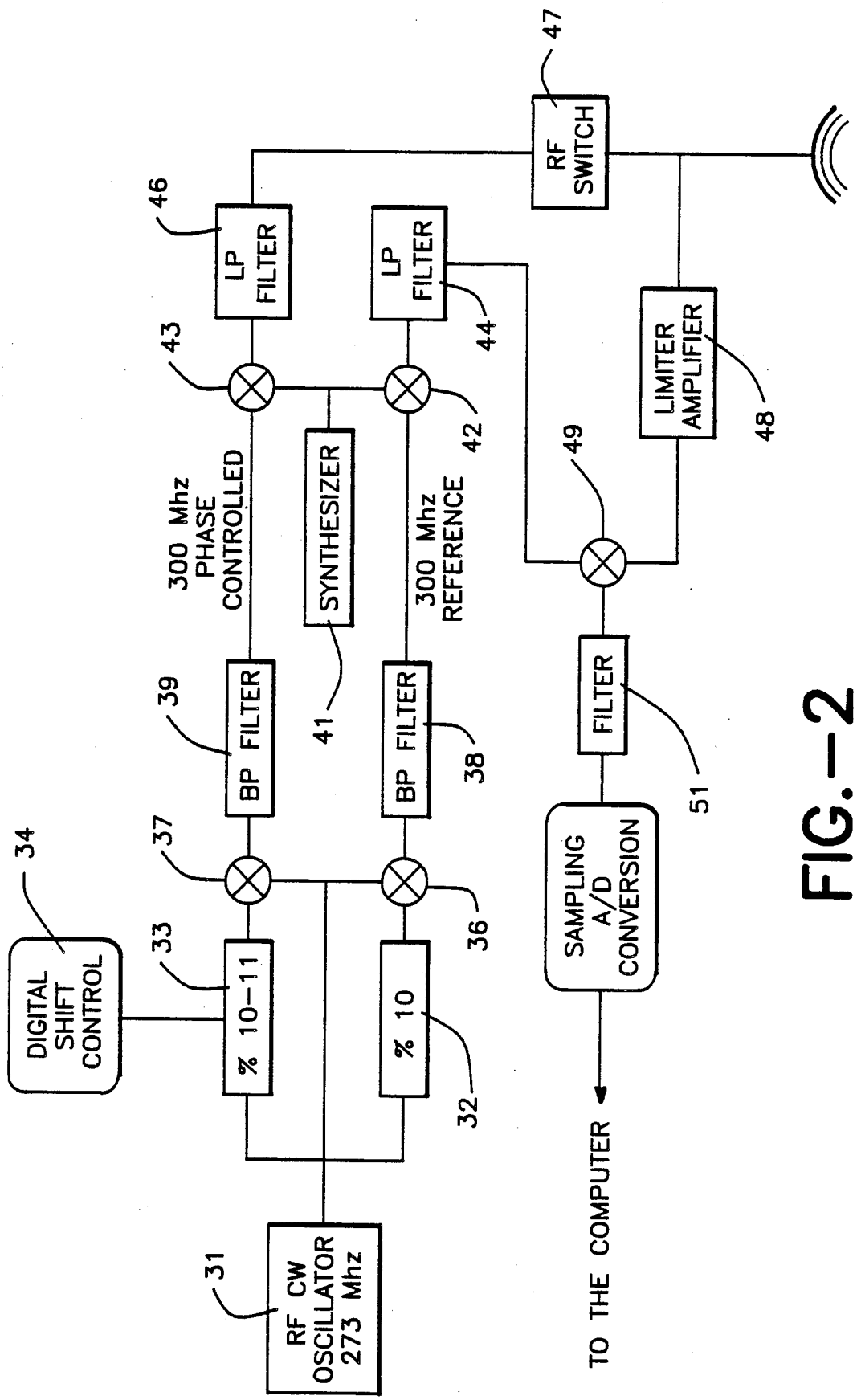
FIG. 2 is a schematic diagram of a electrical circuit suitable for exciting the transducer, receiving signal from the transducer and providing amplitude and phase measurements of the transducer output.

A system for providing reference signals and excitation signals having a controllable relative phase is shown in FIG. 2. Referring to FIG. 2, an RF continuous wave oscillator 31 generates a 273 Mhz signal and applies it to dividers. One divider 32 divides the input signal by 10. The other divider 33 divides by 10 or 11 depending upon the level of a digital shift signal applied to dividers 33 by the digital shift control 34 which may comprise a computer. The 273 Mhz master frequency is generated by a quartz crystal.

Figure 3:
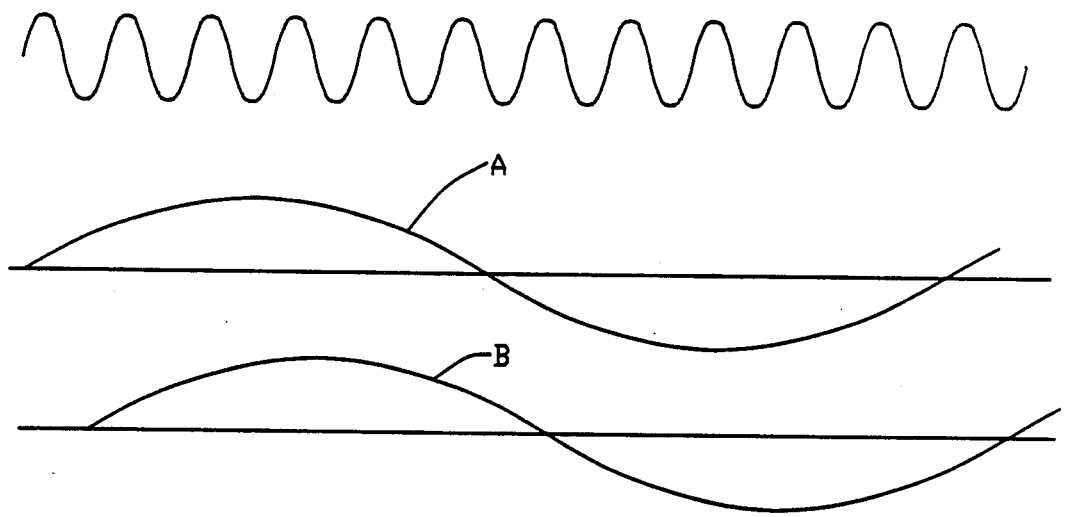
FIG. 3 shows the input signal and the formation of a delayed signal.

The divider 32 is not controlled and simply divides the incoming frequency by 10, ending with an output signal whose first harmonic is 27.3 MHz. The other divider 33 delivers the phase-controlled signal. The divider 33 can divide the incoming signal by 11 instead of by 10 during one period of the output signal. The result of this division is that an additional time delay is added in the outcoming 27.3 MHz signal which is equal to one period of the input frequency (273 MHz) or in this example 36°. This is illustrated in FIG. 3 where the divided signals A and B are shown with the delay. Each of these two 27.3 MHz is amplified and low-pass filtered with a first-order filter, not shown, for noise reduction purposes; it is then mixed with the 273 MHz master frequency at the mixers 36 and 37. Many intermodulation products are actually present at the output of the mixer. Two high-performance narrowband filters 38 and 39 receive the modulation products and remove all the undesirable components and keep only the 300 MHz. The strong filtering provides two clean 300 MHz continuous waves with a harmonic rejection larger than 50 dB. As one signal is the product of a low-frequency, phase-controlled component and the master frequency, we are left with two 300 MHz signals whose relative phase can be controlled at will by amounts of $2*\pi/10$. The two 300 MHz signals are mixed with a frequency-controlled continuous wave from synthesizer 41 by the mixers 42 and 43. Simple low-pass filters 44 and 46 reject the upper band.

Assuming that the synthesizer frequency is tuned to fs in MHz with $fs > 300$ MHz, then we get two phase-controlled signals whose frequencies are $ft = fs - 300$ MHz. These two signals are therefore available in a wide frequency range, typically 1 MHz−200 MHz for 301 MHz $< fs <$ 500 MHz. One of these signals is gated in an RF switch 47 to generate the tone burst that is sent to the transducer. The return echo is then limited, amplified at 48, and mixed at mixer 49 with the reference signal.

If ft is the frequency of operation, R and $\phi$ respectively, the amplitude and the phase relative to the reference of the return echo, then the outcoming signal is proportional to $R\cos(\phi) + F(2*ft)$, where F is a component whose frequency is $2*ft$. This component is removed in a low-pass filter 51, and the DC level that contains the acoustic echo information is sent to a fast sample and hold, and then to an A/D converter.

Figure 4:
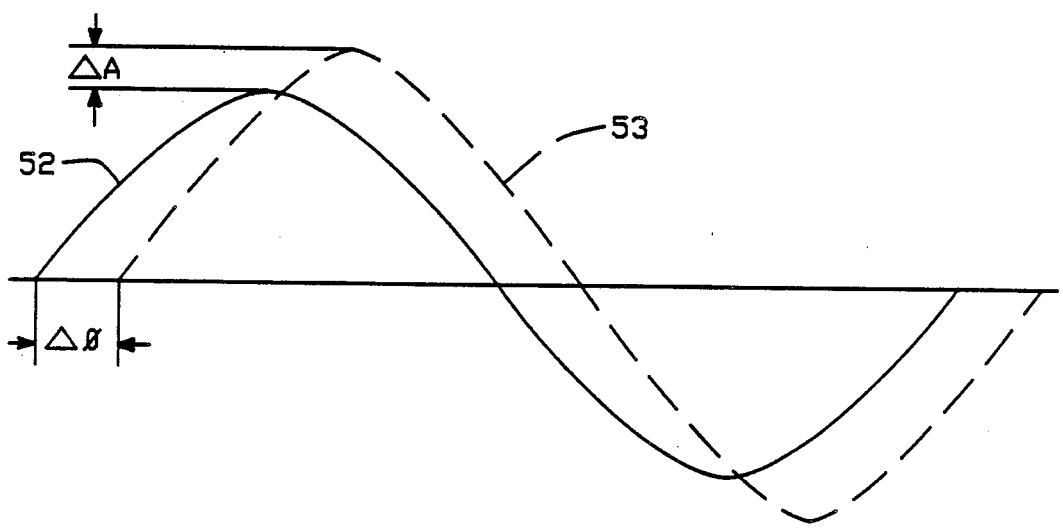
FIG. 4 shows the output for a selected location with and without defects

For measurement or inspection at one location, the reference signal is shifted ten times (five times in high-speed applications) by the digital control 34 and each time a new measurement is made. These values vary sinusoidally with the phase shift, as shown in FIG. 4, and a simple signal processing, which is nothing but a DFT on a few points at one specific frequency, used to extract the first harmonic. This removes, at the same time, DC and higher-order harmonics introduced by the nonlinearities of the system. However, if there is a defect, both the amplitude and phase of the echo will be affected. Thus, if the amplitude and phase of the echo signal is compared to the average $A \angle \phi$ FIG. 4, the defect will be detected. The curves 52 and 53 illustrate defects y showing the difference in amplitude and phase between reference signal 52 and output echo signal 53.

Figure 5:
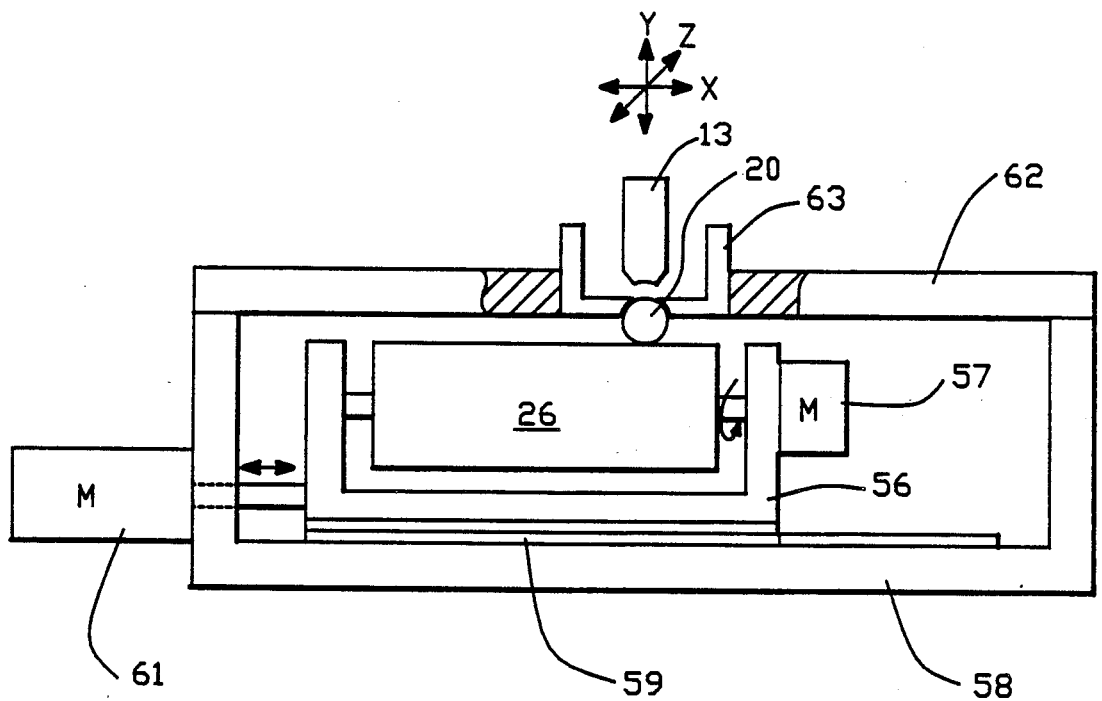
FIG. 5 shows a mechanism for rotating the bearing ball to present surface portions to the transducer.

FIG. 5 schematically illustrates a system for translating and rotating the roller 26 to present all surfaces of the bearing ball to the transducer. The roller includes shafts which extend into bearings, not shown, carried by the roller support 56. A motor 57, which may be a stepper motor, is mounted on the support 56 and rotates the roller by driving one of the roller shafts. By stepping the drive motor successive locations on an equator of bearing ball 20 are presented to the transducer 11. The roller support 56 is mounted as a frame 58 by a linear bearing 59. The roller support is moved on the linear bearing 59 by a linear motor 61, which may be a stepper motor. By stepping the motor 61 the bearing ball is rotated to present a new equator which can then be inspected by the transducer 11. By selectively energizing the motors all locations on the bearing ball surface are presented to the transducer for inspection.

The assembly includes means for restraining the bearing ball and causing it to rotate at a selected location. The frame may include a cover 62 hinged, not shown, to the frame to permit changing of bearing balls. The ball is retained by a retainer 63 which has an opening with outwardly sloping curved sides to receive the upper portion of the bearing ball 20 and allow it to rotate. The transducer is supported on the frame by a support assembly, now shown, which movement of transducer provides for in the three directions shown by the arrows x, y and z to cooperate with the surface of the bearing ball. A coupling liquid is applied between the ball 20 and transducer 11.

Figure 6:
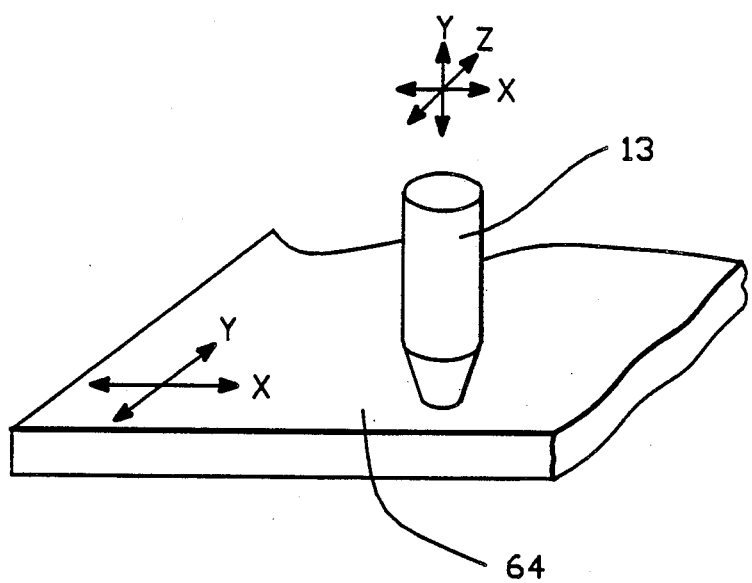
FIG. 6 schematically shows a transducer associated with a flat surface to measure surface defects.

FIG. 6 illustrates the transducer in cooperation with a flat surface which can be moved in the x, z direction to provide a so called raster scan. The transducer is mounted for adjustment and cooperation with the surface. Since means for mounting and moving an object in a raster pattern are known none are shown. Likewise, means are well known for adjustably mounting a transducer and the movement is illustrated by the x, y and z arrows.

The flat surface could engage a bearing ball and present different locations on the ball to a transducer to thereby inspect the surface of the bearing ball. Movement would be in the x,z direction. The flat plate or the roller could be used to rotate a cylindrical bearing and to move the bearing to present different surface locations for inspection.

Figure 7:
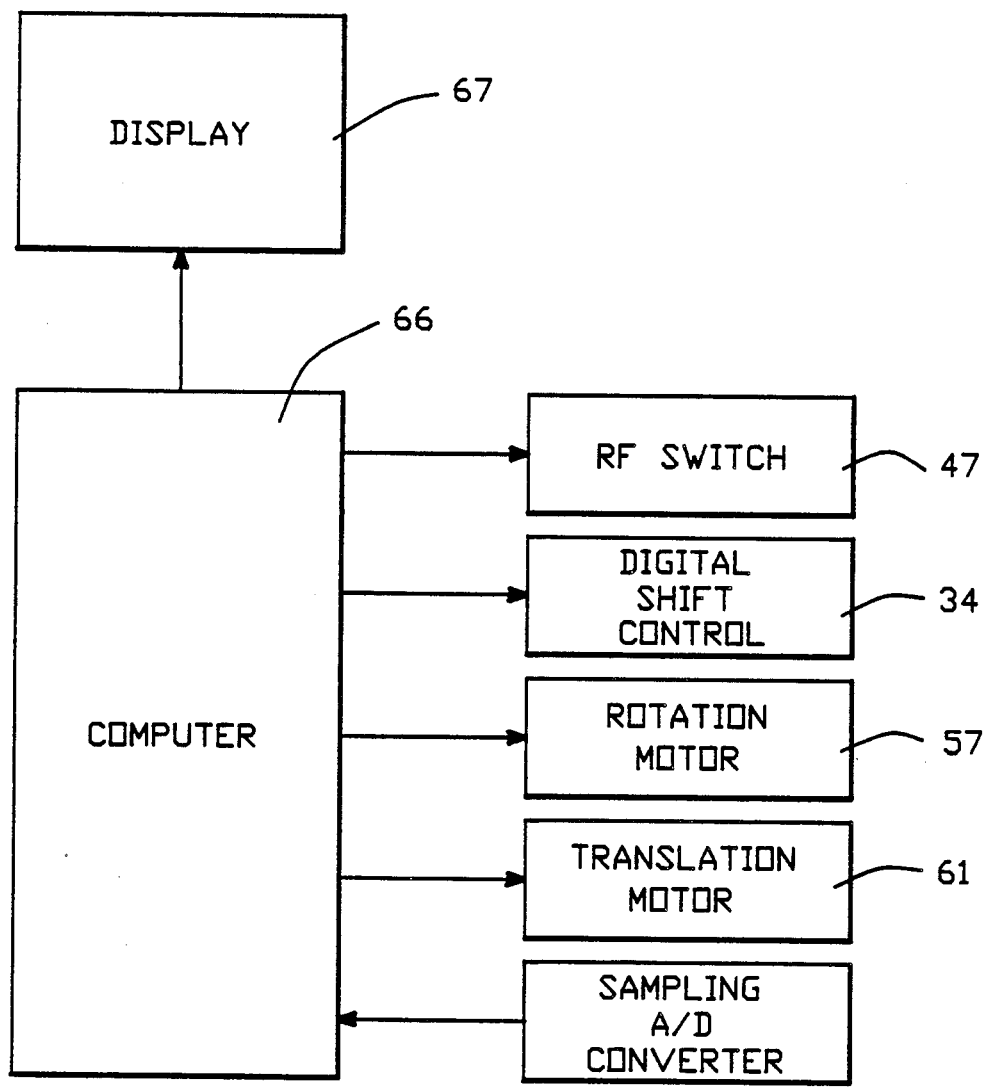
FIG. 7 is a block diagram of a computer control for the invention.

Referring to FIG. 7 the computer control for the bearing ball inspection system is shown schematically. The computer 66 controls the digital shift control 34 so that it steps through the 360° phase shift in synchronism with controlling opening of the RF switch 47 to shift the phase during each burst. The computer controls stepping of the motor 57 to inspect all locations as a given equator and then steps the motor 61 to present a new equator for inspection. This is repeated until all of the bearing surface has been inspected. The computer receives signals from the sampling circuit and averages the amplitude and phase outputs and compares readings to the average to detect flaws such as cracks, gouges or depressions. If desired the surface defects can be displayed on display 67.

Thus, there has been provided an acoustic microscope system and apparatus which permits detection of surface defects on the order of 0.5×0.5 micrometers in size on flat scanned surfaces, on the surface of bearing balls and on the surface of cylindrical bearings.

What is claimed is:

1. An acoustic microscope surface inspection system for detecting surface defects in a test object comprising:
    means for generating pulses of high frequency electrical energy;
    a transducer for receiving said high frequency electrical energy pulses and generating and focusing acoustic wave pulses which impinge at a selected location on the object under test and receiving acoustic wave pulses emanating from said location and generating output signal pulses;
    means for generating a reference electrical signal, at said high frequency;
    means for controlling and incrementally shifting the phase between said reference signal and said high frequency electrical energy pulses at said selected location through 360 electrical degrees; and
    means for receiving said reference signal and said transducer output signal pulses at said selected location and provide an output signal indicative of the difference in amplitude and phase of said reference signal and transducer output signal pulses for each pulse of the pulses at said selected location.

2. A system as in claim 1 including means for presenting different locations of said surface to said transducer.

3. A system as in claim 2 including means for comparing said amplitude and phase of said output signals at different locations.

4. A system as in claims 1, 2 or 3 in which said surface is the surface of a sphere and said means for presenting different locations on the surface comprises a roller which is translated.

5. A system as in claims 1, 2 or 3 in which said surface is the surface of a cylinder.

6. A system as in claims 1, 2 or 3 in which said surface is a flat surface and said means for presenting different locations moves said surface on a plane.

7. A system as in claim 1 in which said test object is a sphere and means are provided for rotating said sphere to sequentially provide test locations along an equator to said transducer and means for rotating said sphere in a different direction to provide different equators to said transducer.

8. A system as in claim 1 in which said means for rotating said sphere comprises a roller which engages said sphere and means for rotating and translating said roller.

9. The method of inspecting the surface of a test object to detect surface defects such as cracks, depressions and gouges comprising the steps of:
    generating first and second high frequency electrical signals of the same frequency and progressively changing the phase relationship in a stepwise manner by small increments between said signals,
    gating said first high frequency electrical signal to provide pulses of high frequency electrical energy,
    generating from said pulses of high frequency electrical energy acoustic pulses applied to the surface of said test object at selected locations,
    detecting acoustic energy pulses emanating from said selected locations responsive to said acoustic pulses and providing output electrical signal pulses,
    processing said output electrical signal pulses and said second high frequency signal to generate outputs having an amplitude and phase representative of the difference in amplitude and phase between said second frequency signal and the amplitude and phase of each of said output electrical signal pulses at said selected location.

10. The method as in claim 9 in which the phase of said first and second high frequency electrical signals is shifted through 360° for each of said selected locations.

11. A method as in claim 10 in which the output for different locations is compared.

* * * * *